(12) United States Patent
Close et al.

(10) Patent No.: US 8,870,840 B2
(45) Date of Patent: Oct. 28, 2014

(54) PROTECTIVE DIAPERING SYSTEM

(75) Inventors: Clare E. Close, Henderson, NV (US); Maria Eres G. Navajas Sombito, Henderson, NV (US)

(73) Assignee: Protective Diaper, LLC, Henderson, NV (US)

(*) Notice: Subject to any disclaimer, the term of this patent is extended or adjusted under 35 U.S.C. 154(b) by 198 days.

(21) Appl. No.: 13/171,702

(22) Filed: Jun. 29, 2011

(65) Prior Publication Data
US 2013/0006208 A1    Jan. 3, 2013

(51) Int. Cl.
*A61F 13/471*    (2006.01)
*A61F 13/491*    (2006.01)
*A61F 13/495*    (2006.01)

(52) U.S. Cl.
CPC ........... *A61F 13/471* (2013.01); *A61F 13/4915* (2013.01); *A61F 13/495* (2013.01)
USPC ....................... 604/385.09; 604/389; 604/391

(58) Field of Classification Search
USPC .............. 604/385.09, 385.201, 389, 390, 391
See application file for complete search history.

(56) References Cited

U.S. PATENT DOCUMENTS

| | | | |
|---|---|---|---|
| 4,850,988 A * | 7/1989 | Aledo et al. | 604/385.21 |
| 5,383,867 A | 1/1995 | Klinger | |
| 5,618,279 A | 4/1997 | Pudlo | |
| 5,716,350 A | 2/1998 | Ryan | |
| 5,843,065 A | 12/1998 | Wyant | |
| 5,853,403 A | 12/1998 | Tanzer et al. | |
| 5,906,602 A | 5/1999 | Weber et al. | |
| 6,129,719 A * | 10/2000 | Nozaki et al. | 604/385.01 |
| 6,152,908 A | 11/2000 | Widlund et al. | |
| 6,817,992 B1 * | 11/2004 | Sassak et al. | 604/385.09 |
| 6,979,325 B2 | 12/2005 | Reddy | |
| 7,918,838 B2 | 4/2011 | Minato et al. | |
| 8,142,407 B2 | 3/2012 | Reddy | |
| 2004/0087919 A1 | 5/2004 | Tanaka et al. | |
| 2004/0143232 A1 | 7/2004 | Perez et al. | |
| 2007/0225670 A1 | 9/2007 | Connell | |
| 2007/0239128 A1 | 10/2007 | Takada et al. | |
| 2011/0060306 A1 | 3/2011 | Otsubo | |
| 2011/0066125 A1 | 3/2011 | Otsubo | |
| 2011/0184371 A1 | 7/2011 | Sakaguchi | |

FOREIGN PATENT DOCUMENTS

| | | |
|---|---|---|
| EP | 0 955 028 A2 | 11/1999 |
| EP | 1 767 176 A1 | 3/2007 |
| EP | 2 098 202 A1 | 9/2009 |
| JP | H08 322878 | 12/1996 |
| JP | 10005262 A | 1/1998 |
| JP | 2005168967 A | 6/2005 |

OTHER PUBLICATIONS

International Search Report; International Application No. PCT/US2012/043608, Aug. 28, 2012.

* cited by examiner

*Primary Examiner* — Tan-Uyen (Jackie) T Ho
*Assistant Examiner* — Peter S Vasat
(74) *Attorney, Agent, or Firm* — Thomas J. Connelly; Wilhelm Law, S.C.

(57) ABSTRACT

A protective diapering system is provided for the prevention of migration and introduction of stool with a male's genital area. The protective diapering system including a diaper having an anterior flap, a posterior flap, and a fenestrated flap disposed between the anterior and posterior flaps.

21 Claims, 4 Drawing Sheets

PROTECTIVE DIAPERING SYSTEM

FIELD

The embodiments provided herein relate generally to diapers, and more particularly to a protective diapering system that facilitates the prevention of stool soiling of a user's genital area.

BACKGROUND INFORMATION

Current diaper designs maximize urine absorption but do not function to keep stool from soiling a user's genitalia. In certain situations, when a male infant's stool is introduced and comes into contact with his genitalia, the effects can be quite harmful. By way of example, male infants undergoing pediatric circumcision, hypospadias surgery, and other similar forms of penile surgery are at a high risk for dressing and wound contamination from stool soiling in the diaper. In such penile surgical situations, surgical dressings are placed on the penis to control and prevent post-operative bleeding and to minimize the risk of infection. The dressing should be kept dry for two to five days to allow healing of the surgical site. If the dressing becomes stool soiled, early rinsing of the dressing or removal of the dressing is necessary to prevent infection from entrapped stool. Aside from the problem of early rinsing or removal of penile surgical dressing, the inability to keep the post-operative genital site clean can result in very harmful consequences such as infection, inflammation, or additional scarring. In turn, these consequences may require additional surgeries.

In addition to complications arising in post-operative situations, it is also harmful for stool and waste material to remain in contact with the male genitalia for a prolonged period of time. For example, male infants are at risk for infection of the foreskin or urinary tract in non-surgical situations, and even adult males are at risk for infections of the foreskin or urinary tract when they utilize a diaper-like product when faced with bowel and bladder incontinence. Stool contact with the male genitalia is a very common problem because there are no barriers preventing the stool migration to the genital region when a conventional absorbent diaper is used. When the stool migrates to the male genitalia region, caregivers find it difficult and time consuming to effectively clean the soiled areas. Like post-operative situations, if the stool remains in contact with the male genitalia, potential harmful consequences may result, such as urinary tract infections, or inflammation of the male genitalia.

Currently there are no commercial diaper products available that address these problems. To overcome these problems, an improved protective diapering system is desirable.

SUMMARY

The embodiments provided herein are directed to a protective diapering system capable of separating and protecting a male's penis from the migration and introduction of stool to the male's genital area. In a preferred embodiment, the protective diapering system comprises a diaper and a fenestrated flap, wherein the diaper comprises an anterior flap and a posterior flap, and further wherein the fenestrated flap is disposed between the anterior flap and the posterior flap of the diaper.

In one embodiment, the diaper of the protective diapering system has an outer surface and an inner surface, wherein the outer surface and inner surface can be constructed with conventional diaper material. For example, the outer surface can be constructed with a waterproof material capable of preventing any bodily discharge from seeping out of the diaper, and the inner surface can be constructed with conventional absorbent filler material capable of absorbing bodily discharge, i.e., urine and stool.

In one embodiment, the diaper can be configured in a substantially hour-glass shape having a generally rectangular shaped cross-sectional area at the top and bottom of the hour-glass and having both lateral sides of the diaper tapered down from both the top and bottom of the hour-glass along curvilinear edges, thereby forming a reduced cross-sectional area at an approximate midline of the diaper. The anterior flap and the posterior flap are each configured to comprise opposite halves of the hour-glass shaped diaper, each having generally trapezoidal shapes with curvilinear lateral edges.

In one embodiment, the fenestrated flap can be configured to have an anterior surface, a posterior surface, a bottom end, a top end, a first lateral side, and a second lateral side; and the fenestrated flap can be configured in a shape substantially similar to the shapes of the anterior flap and posterior flap of the diaper, i.e., the fenestrated flap can be configured in a substantially half hour-glass shape having a generally trapezoidal shape with curvilinear lateral edges.

In one embodiment, the fenestrated flap can be made of a thin waterproof membrane covered with conventional absorbent diaper material. The thin waterproof membrane can be made with a polyethylene material or hydrophobic nonwoven material. The conventional absorbent diaper material can be made with hydrophilic nonwoven material, absorbent polymer material, or a mixture of air-laid paper and superabsorbent polymers.

In one embodiment, the fenestrated flap is configured to attach to the inner surface of the diaper where the bottom end of the fenestrated flap is sewn onto the diaper along the approximate midline between the anterior flap and the posterior flap.

In one embodiment, the fenestrated flap is configured with a longitudinal slit, which begins from the top end of the fenestrated flap, continues in a longitudinal direction towards the bottom end of the fenestrated flap, and terminates at a fenestration. In order for the fenestrated flap and the fenestration to comfortably receive the user's penis, it is appreciated that the fenestration flap and fenestration can be configured in a variety of shapes and sizes, which can vary based on conventional body-type measurements of the user, such as height, weight, waist size, and even age.

In one embodiment, the fenestrated flap can be configured with fastening tabs capable of bridging the longitudinal slit and fastening the two parts of the fenestrated flap, which are created by the longitudinal slit. In a preferred embodiment, the fastening tabs are coupled to the anterior surface of the fenestrated flap to prevent the chaffing and irritation that may be caused if the fastening tabs contact the abdomen of the male infant. In a preferred embodiment, the fastening tabs are configured with a material, such as an adhesive, that will complement the material of the anterior surface thereby facilitating a suitable and sufficient attachment of the fastening tabs and the fenestrated flap.

To dress a male infant with the protective diapering system, the male infant is initially placed in the posterior compartment of the protective diapering system with the male infant's bottom or posterior against the posterior flap and the fenestrated flap and the anterior flap positioned between the male infant's legs. The fastening tabs are opened to allow the male infant's penis to be placed through the fenestration of the fenestration flap. When the male infant's penis is received through the fenestration, the fastening tabs are then adjusted and closed such that the fenestration flap provides a waterproof barrier around the surrounding portions of the male infant's penis. When the male infant's penis is received by the fenestration and the fenestrated flap surrounds the outer portions of the male infant's penis, the anterior compartment is intended to only receive urine and the posterior compartment is intended to only receive stool. As such, the fenestration flap acts as a barrier between the anterior compartment and the posterior compartment such that the male infant's stool is prevented from migrating towards, and possibly infecting, the male infant's genital area.

In one embodiment, the anterior flap, the fenestrated flap, and the posterior flap are configured with pulling and securing tabs capable of securing the protective diapering system around the male infant. In one embodiment, the pulling tabs of the fenestrated flap are used to draw the fenestrated flap toward and/or against the infant male's abdomen and are tucked behind the infant male. One set of securing tabs of the posterior flap are configured with coupling material, such as, e.g., adhesive, and are long enough to attach to the diaper material of the anterior surface of the fenestrated flap to facilitate a secured closure of the fenestrated flap with the posterior flap. Similarly, the pulling tabs of the anterior flap are used to draw the anterior flap toward the infant male's abdomen and are tucked behind the infant male. A second set of securing tabs of the posterior flap are configured with coupling material, such as, e.g., adhesive, and are long enough to attach to the diaper material of the anterior surface of the anterior flap to facilitate a secured closure of the anterior flap with the posterior flap. In another embodiment, the first and second set of securing tabs of the posterior flap comprise a hook and loop material and the anterior surface of the fenestrated flap and the anterior flap comprise a material to which the hook and loop material of the first and second set of securing tabs can adhere.

In one embodiment, the diaper and the fenestrated flap may be configured with elastic material on both lateral sides of the approximate intersection midline of the diaper, which allows for comfort and support when the protective diapering system is used on a male infant.

Other systems, methods, features, and advantages of the example embodiments will be or will become apparent to one with skill in the art upon examination of the following figures and detailed description.

BRIEF DESCRIPTION OF THE FIGURES

The details of the embodiments, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

DETAILED DESCRIPTION

The embodiments provided herein are directed to a protective diapering system capable of separating and protecting the male's penis from the migration and introduction of stool to the male's genital area. The descriptions below commonly reference a male infant as the user of the protective diapering system. Such references are not intended to limit the scope of the present invention. Rather, all references and illustrations are intended to convey the concepts and attributes of the various embodiments and it should be understood that the invention is not to be limited to the particular references, illustrations, or embodiments disclosed.

Figure 1:
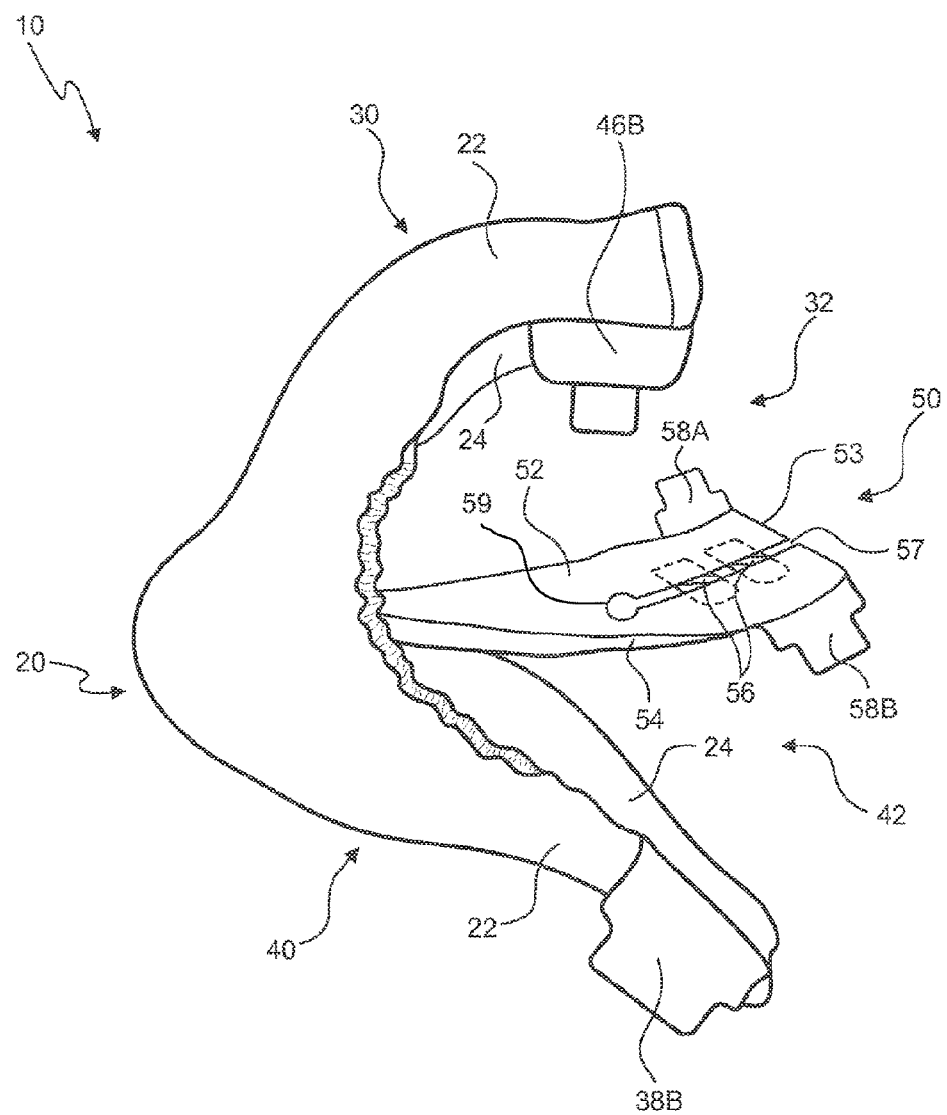
FIG. 1 is an illustration of a perspective view of one embodiment of a protective diapering system.

FIG. 1 illustrates a perspective view of one embodiment of the protective diapering system 10. As illustrated in FIG. 1, the protective diapering system 10 comprises a diaper 20 and a fenestrated flap 50. In one embodiment, the diaper 20 can be configured with conventional component parts and materials of a conventional disposable diaper.

As depicted, the diaper 20 comprises an outer surface 22 and an inner surface 24. In one embodiment, the outer surface 22 can be constructed of a conventional waterproof material capable of preventing bodily discharge from seeping out of the diaper 20. By way of example, the outer surface 22 can be constructed with a polyethylene material that is capable of preventing leakage out of the diaper 20. In another embodiment, the outer surface 22 can be given a cloth-like appearance by adding a thin polypropylene non-woven sheet to a cloth film. It is appreciated that the outer surface 22 may be constructed with other suitable materials capable of serving the purpose of preventing leakage of bodily discharge, such as urine and stool, when the protective diapering system 10 is in use.

In one embodiment, the inner surface 24 can be constructed with conventional layers comprising a surface layer that is in contact with the infant's skin, a distribution layer directly beneath the surface layer, and an inner absorbent layer. According to conventional configurations of a disposable diaper, the surface layer can be made with a hydrophilic nonwoven material that allows the infant's discharged urine to flow into the other layers of the inner surface 24 of the diaper 20. The distribution layer can be made with either through air bond (TAB) nonwovens, curly fibers, or some other types of high-loft nonwoven materials. The inner absorbent layer can be made with a super absorbent polymer or a mixture of air-laid paper and superabsorbent polymers. It is appreciated that the component parts and materials used to construct the inner surface 24 can be varied according to other well-known and conventional methods and materials to carry out the main purpose of the inner surface 24, which is to adequately absorb typical bodily discharge, such as urine and stool, when the protective diapering system 10 is in use.

The diaper 20 preferably comprises an anterior flap 30 and a posterior flap 40, as illustrated in FIG. 1. In one embodiment, the anterior flap 30 is configured with pulling tabs 38A (see FIG. 2). 38B and the posterior flap is configured with outer securing tabs 46A (see FIG. 2), 46B, which are capable of securing to the anterior flap 30 to secure the diaper 20 around the male infant, as explained in greater detail below. The pulling tabs 38A, 38B of the anterior flap 30 are formed of diapering material or other non-coupling or non-adhesive material. The outer securing tabs 46A, 46B of the posterior flap 40 are constructed with coupling material such as, e.g., an adhesive, and are long enough to attach to the diaper material of the anterior surface of the anterior flap 30 to facilitate a secured closure between the anterior and posterior flaps 30 and 40. Alternatively, the outer securing tabs 46A, 46B can comprise hook and loop material or other suitable material. The pulling tabs 38A, 38B of the anterior flap 30 and the outer securing tabs 46A, 46B of the posterior flap 40 can also be made with elastic materials, such as polyurethane, polyester foam, synthetic rubber, or spandex.

Figure 2:
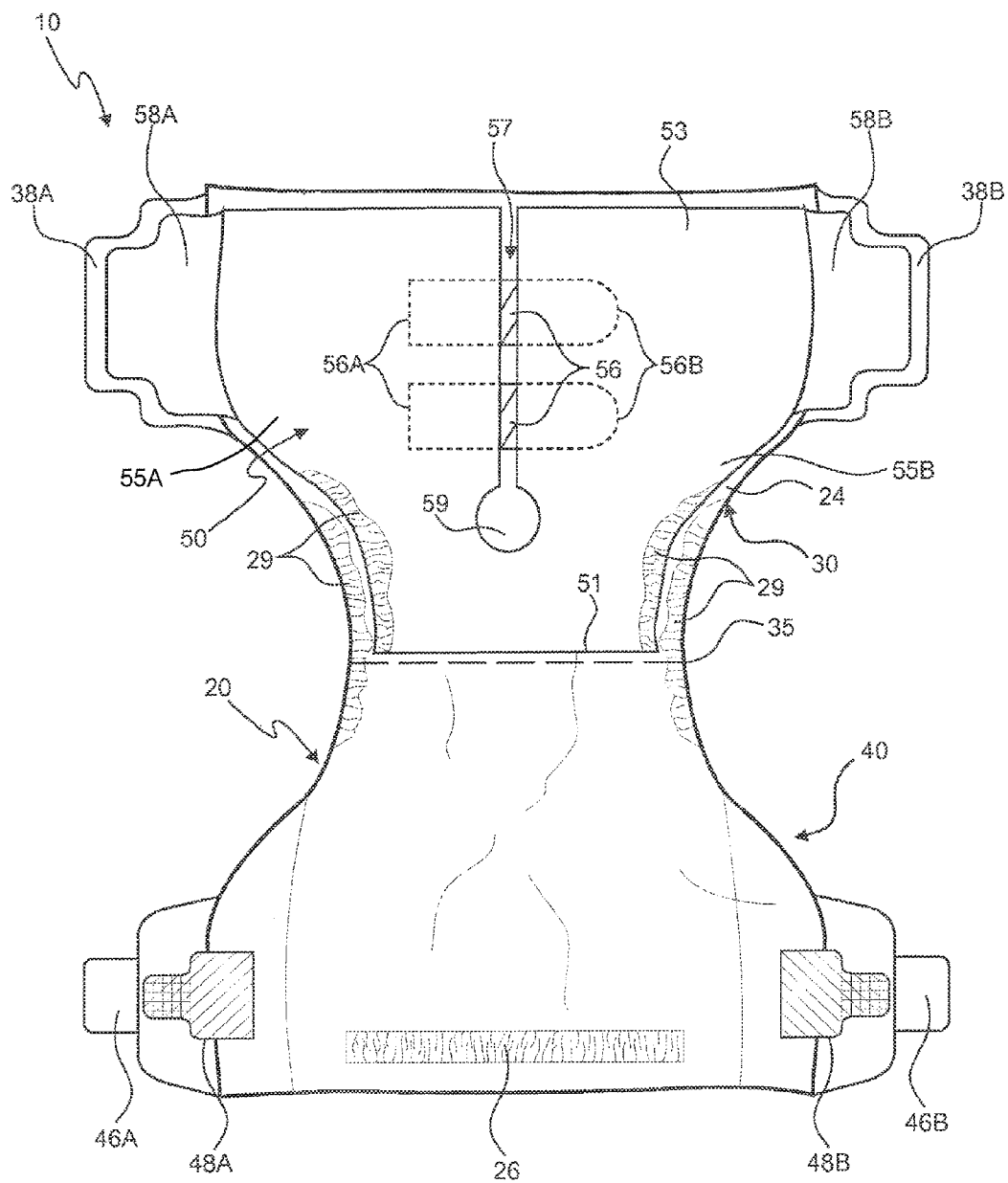
FIG. 2 is an illustration of a plan-view depiction of the protective diapering system in an open-state, where the inner surface of a diaper of the protective diapering system is predominantly shown.

FIG. 2 illustrates a plan-view depiction of the protective diapering system 10 in an open-state, where the inner surface 24 of the diaper 20 is shown. As illustrated in FIG. 2, the diaper 20 is configured in a substantially hour-glass shape having a generally rectangular shaped cross-sectional area at the top and bottom of the hour-glass and having both lateral sides of the diaper 20 tapered down from both the top and bottom of the hour-glass along curvilinear edges, thereby forming a reduced cross-sectional area at an approximate midline 35 of the diaper 20. When the diaper 20 is closed, the cross-sectional area at the top and bottom of the hour-glass, as illustrated in FIGS. 1-2, correspond to part of the diaper 20 that fits around the male infant's waist and the reduced cross-sectional area of the diaper 20 correspond to the area where the male infant's legs are positioned.

As illustrated in FIG. 2, the anterior flap 30 and the posterior flap 40 are each configured to comprise opposite halves of the hour-glass shaped diaper 20, each having generally trapezoidal shapes with curvilinear lateral edges. Also as illustrated in FIG. 2, the anterior flap 30 and the posterior flap 40 intersect at the approximate midline 35 of diaper 20. It is appreciated that according to conventional disposable diaper configurations, the inner surface 24 of the anterior flap 30 may be constructed with a greater amount of absorbent filler material than the inner surface 24 of the posterior flap 40 to accommodate for the higher typical output of urine as compared to the typical output of stool. Under such a configuration, the thickness of the anterior flap 30 is greater than the thickness of the posterior flap 40. It is appreciated that the diaper 20 can be configured according to conventional configurations of disposable diapers that are adequately absorbent to accept typical urine and stool output.

Figure 3:
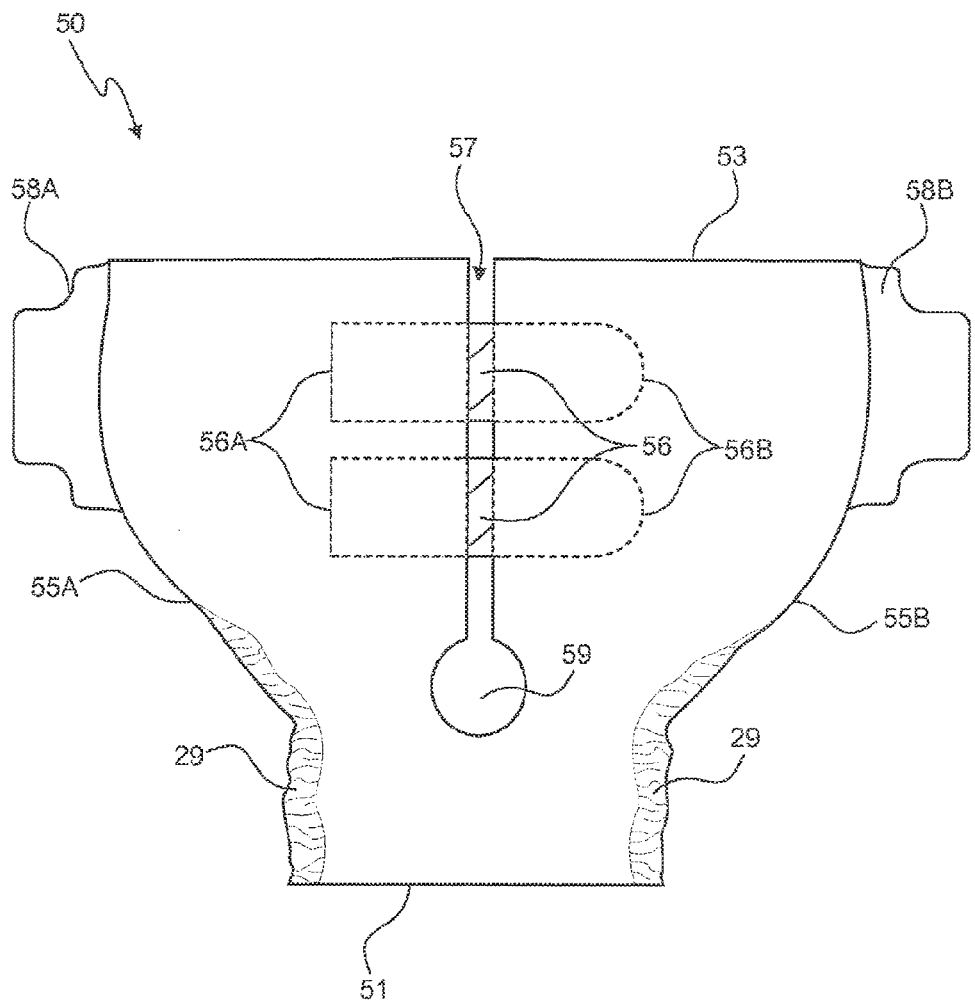
FIG. 3 is an illustration of a plan-view depiction of a fenestrated flap of the protective diapering system, which has been removed from the diaper of the protective diapering system.

In a preferred embodiment, the fenestrated flap 50 is disposed between the anterior flap 30 and the posterior flap 40, as illustrated in FIGS. 1-2. FIG. 3 illustrates a plan-view depiction of the fenestrated flap 50, which has been removed from the diaper 20. As illustrated in FIGS. 1-3, the fenestrated flap 50 has an anterior surface 52 (see FIG. 1), a posterior surface 54 (see FIG. 1), a bottom end 51, a top end 53, a first lateral side 55A, and a second lateral side 55B. In one embodiment, the fenestrated flap 50 can be configured in a shape substantially similar to the shape of the anterior flap 30 and the posterior flap 40 of the diaper 20. In other words, according to one embodiment, the fenestrated flap 50 can be configured in a substantially half hour-glass shape, which can be described as a generally trapezoidal shape with curvilinear lateral edges tapered down from the top end 53 to the bottom end 51, as illustrated in FIGS. 2-3. It is appreciated that the fenestrated flap 50 can be configured in a variety of different shapes. By way of example, the fenestrated flap 50 can be shaped in a circular, rectangular, or trapezoidal fashion.

As explained in further detail below, the fenestrated flap 50 is configured to function as a barrier to prevent a male infant's stool from migrating to and soiling the male infant's genital area. In one embodiment, the fenestrated flap 50 comprises a thin waterproof membrane covered with a thin layer of conventional absorbent diaper material. The thin waterproof membrane can be made with a polyethylene material or hydrophobic nonwoven material. The conventional absorbent diaper material can be made with hydrophilic nonwoven material, absorbent polymer material, or a mixture of air-laid paper and superabsorbent polymers. It is appreciated that the fenestrated flap 50 can be made with other suitable materials to carry out the main purpose of the fenestrated flap 50, which is to prevent stool from migrating to the male infant's genital area In one embodiment, the fenestrated flap 50 is configured with pulling tabs 58A, 58B. Also, the posterior flap 40 can be configured with inner securing tabs 48A, 48B which are securable to the fenestrated flap 50 to secure the fenestrated flap 50 with the posterior flap 40 around the male infant's waist. The pulling tabs 58A, 58B of the fenestrated flap 50 are formed of diapering material or other non-coupling or non-adhesive material. The inner securing tabs 48A, 48B of the posterior flap 40 are constructed with coupling material such as, e.g., an adhesive, and are long enough to attach to the diaper material of the anterior surface of the fenestrated flap 50 to facilitate the secured closure between the fenestrated and posterior flaps 50 and 40. Alternatively, the inner securing tabs 48A, 48B can comprise hook and loop material, or other suitable material. The pulling tabs 58A, 58B of the fenestrated flap 50 and the inner securing tabs 48A, 48B of the posterior flap 40 can also be made with elastic materials, such as polyurethane, polyester foam, synthetic rubber, or spandex.

In one embodiment, the fenestrated flap 50 is configured to attach to the inner surface 24 of the diaper 20, whereby the bottom end 51 of the fenestrated flap 50 is attached along the approximate midline 35 of the diaper 20. In one embodiment, the fenestrated flap 50 is sewn to the inner surface 24 of the diaper 20 along the approximate midline 35. In another embodiment, the fenestrated flap 50 is attached by an adhesive to the inner surface 24 of the diaper 20 along the approximate midline 35. It is appreciated that the fenestrated flap 50 can be configured to attach to the inner surface 24 of the diaper 20 by a variety of methods. It is also appreciated that the fenestrated flap 50 can be attached to the inner surface 24 of the diaper 20 in various locations. By way of example, the bottom end 51 of the fenestrated flap 50 can be attached to the inner surface 24 along a line offset from the approximate midline 35. In other words, the fenestrated flap 50 may be coupled to the diaper 20 such that the anterior flap 30 and the posterior flap 40 are of substantially equal sizes, or alternatively, different sizes. As explained in further detail below, and as illustrated in FIG. 1, the protective diapering system 10 can comprise an anterior compartment 32 and a posterior compartment 42, which are produced from the attachment of the fenestrated flap 50 to the diaper 20. It is appreciated that the various locations at which the fenestrated flap 50 is attached to the inner surface 24 of the diaper 20 can create an anterior compartment 32 and a posterior compartment 42 of equal or different sizes.

In one embodiment, the fenestrated flap 50 is configured with a longitudinal slit 57, which, as illustrated in FIGS. 2-3, begins from the top end 53 of the fenestrated flap 50, continues in a longitudinal direction towards the bottom end 51 of the fenestrated flap 50, and terminates at a fenestration 59. In one embodiment, the fenestration 59 is located at a position near, but before, the bottom end 51 of the fenestrated flap 50. In a preferred embodiment, the fenestration 59 is located at a position that corresponds to the position of the male infant's penis when the protective diapering system 10 is in use. As illustrated in FIGS. 1-3, the fenestration 59 can configured in a substantially circular shape. However, in order for the fenestrated flap 50 and the fenestration 59 to comfortably receive the user's penis, it is appreciated that the fenestration flap 50 and fenestration 59 can be configured in a variety of shapes and sizes, which can vary based on conventional body-type measurements of the user, such as height, weight, waist size, and even age. In other words, the fenestration flap 50 and the fenestration 59 of an infant's protective diapering system 10 will be relatively smaller than the fenestration flap 50 and the fenestration 59 of an adult male's protective diapering system 10.

As illustrated in FIGS. 1-3, the fenestrated flap 50 can also be configured with fastening tabs 56 capable of bridging the longitudinal slit 57 and fastening the two parts of the fenestrated flap 50, which are created by the longitudinal slit 57. In a preferred embodiment, the fastening tabs 56 are configured to the anterior surface 52 of the fenestrated flap 50 to prevent chaffing and irritation that may result if the fastening tabs 56 contact the abdomen of the male infant. The fastening tabs 56 can be configured with a variety of materials capable of fastening the two parts of the fenestrated flap 50. In a preferred embodiment, the fastening tabs 56 are configured with a material that will complement the material of the anterior surface 52 thereby facilitating a suitable and sufficient attachment of the fastening tabs 56 to the fenestrated flap 50. By way of example, the fastening tabs 56 are configured with adhesive materials. Alternatively, the fastening tabs 56 can include hook and loop material and the anterior surface 52 can be configure with suitable complementary material. In another embodiment, the fastening tabs 56 may be permanently attached to the fenestrated flap at one end 56A of the fastening tabs 56 and may be configured with a fastening material at an opposite end 56B capable of coupling with the anterior surface 52 of the fenestrated flap 50. When a male infant wears the protective diapering system 10, as explained in further detail below, the fenestration 59 is adjusted around the penis of the male infant and the longitudinal slit 57 is closed above the penis of the male infant by way of the fastening tabs 56.

As illustrated in FIG. 1, the protective diapering system 10 can be configured with the fenestrated flap 50 attached to the inner surface 24 of the diaper 20, thereby creating an anterior compartment 32 and a posterior compartment 42. To dress a male infant with the protective diapering system 10, the male infant is initially placed in the posterior compartment 42 of the protective diapering system 10 with the male infant's bottom or posterior against the posterior flap 40 and the fenestrated flap 50 and the anterior flap 30 positioned between the male infant's legs. The fastening tabs 56 of the fenestrated flap 50 are opened to allow the male infant's penis to be placed through the fenestration 59 of the fenestration flap 50. When the male infant's penis is comfortably received by the fenestration 59, the fastening tabs 56 are then adjusted and closed. With the fenestrated flap 50 secured about the male infant's penis, the pulling tabs 58A, 58B of the fenestrated flap 50 are pulled to draw the fenestrated flap toward and/or against the infant male's abdomen and then the tabs 58A, 58B are tucked behind the infant male. The inner securing tabs 48A, 48B of the posterior flap 40 are drawn over and attached to the diaper material of the anterior surface of the fenestrated flap 50 to facilitate a secured closure of the fenestrated flap 50 with the posterior flap 40. The pulling tabs 38A, 38B of the anterior flap 30 are then used to draw the anterior flap 30 toward the infant male's abdomen and are tucked behind the infant male. The outer set of securing tabs 46A, 46B of the posterior flap 40 are drawn over and attached to the diaper material of the anterior surface of the anterior flap 30 to facilitate a secured closure of the anterior flap 30 with the posterior flap 40. With a secured closure between the posterior flap 40 and the fenestrated and anterior flaps 50 and 30, the fenestrated flap 50 provides a waterproof barrier around the surrounding portions of the male infant's penis. When the male infant's penis is received by the fenestration 59 and the fenestrated flap 50 surrounds the outer portions of the male infant's penis, the anterior compartment 32 is intended to only receive urine and the posterior compartment 42 is intended to only receive stool. With the male infant's penis received through the fenestration 59 and the fenestrated flap 50 secured as discussed below, the male infant's penis extends into the anterior compartment 32 and the fenestration flap 50 acts as a barrier between the anterior compartment 32 and the posterior compartment 42 such that the male infant's stool is prevented from migrating towards, and possibly infecting, the male infant's genital area.

In use, the anterior compartment 32 and the posterior compartment 42 are designed and configured to act as separate chambers for the male infant's urine and stool, respectively. In other words, the fenestrated flap 50 of the protective diapering system 10 is preferably designed and configured to act as a barrier to separate and protect the penis from stool soiling.

Figure 4:
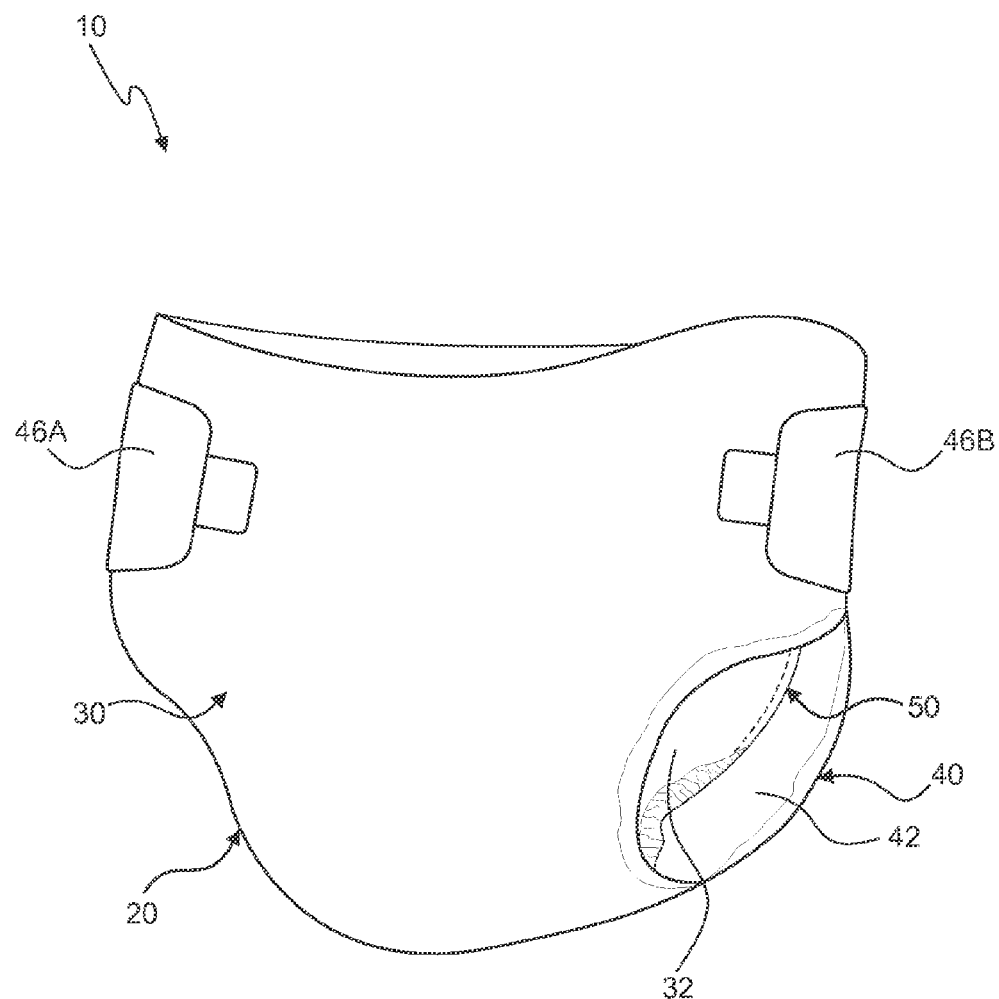
FIG. 4 is an illustration of a perspective view of one embodiment of the protective diapering system in a closed state.

FIG. 4 illustrates a perspective view of one embodiment of the protective diapering system 10 in a closed state. As illustrated in FIG. 4, and as explained in detail above, the protective diapering system 10 is configured to securely fit on a male infant.

In one embodiment, as illustrated in FIGS. 2 & 4, the diaper 20 may be configured with elastic material 29 on both lateral sides of the diaper 20 near the approximate midline 35 of the diaper 20. According to the present embodiment, when the protective diapering system 10 is in use, the elastic material 29 is capable of providing comfort and support around the male infant's upper legs. The fenestrated flap 50 may also be configured with elastic material 29 on both lateral sides of the fenestrated flap 50 near the base of bottom end 51. When the present embodiment of the protective diapering system 10 is in use, the elastic material 29 of the fenestrated flap 50 is also capable of providing comfort and support around the male infant's upper legs. In one embodiment, the diaper 20 may also be configured with elastic material 26 at the peripheral ends of the diaper 20, which may be capable of providing comfort and support around the male infant's waist.

The embodiments of the protective diapering system 10 described herein are directed to its use on male infant's who have gone through circumcision surgery and other related penile surgeries. However, it is appreciated that the protective diapering system 10 can also be used on patients recovering from other surgeries. By way of example, the protective diapering system 10 can be used on patients who have undergone hernia, colon, bowel, or other gastrointestinal related surgeries. Additionally, the protective diapering system 10 can be used on patients who have undergone nephrectomy surgery or other urologic related surgeries.

While the embodiments described herein are susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A protective diapering system, comprising:
 a) a diaper having an outer surface and all inner surface, and having an anterior flap and a posterior flap;

b) a fenestrated flap disposed between said anterior flap and said posterior flap and attached to said inner surface, said fenestrated flap having an anterior surface, a pair of lateral sides, and a first pair of pulling tabs secured to said pair of lateral sides, said first pair of pulling tabs formed from nonadhesive material;

c) a second pair of pulling tabs secured to said anterior flap, said second pair of pulling tabs formed from non-adhesive material; and d) a pair of inner securing tabs and a pair of outer securing tabs secured to said posterior flap and coaxially aligned to one another, said pairs of inner and outer securing tabs constructed from coupling material, said pair of inner securing tabs engaging with said anterior surface of said fenestrated flap to secure said posterior flap thereto, and said pair of outer securing tabs engaging with said anterior flap to secure said posterior flap thereto and thereby secure said diaper to a male user.

2. The protective diapering system of claim 1 wherein said fenestrated flap comprises a slit and a fenestration, and when said protective diapering system is worn by a male user, said fenestrated flap is configured to receive the male user's genital area through said fenestration.

3. The protective diapering system of claim 2 wherein said fenestrated flap further comprises at least one fastening tab configured to bridge said slit.

4. The protective diapering system of claim 1 wherein said fenestrated flap is a thin waterproof membrane covered by an absorbent.

5. The protective diapering system of aim 1 wherein said fenestrated flap is sewn into said diaper.

6. The protective diapering system of claim 1 wherein said fenestrated flap is attached by adhesive onto said diaper.

7. The protective diapering system of claim 1 wherein said fenestrated flap has a trapezoidal shape with curvilinear lateral edges.

8. The protective diapering system of claim 1 wherein said pair of lateral sides of said fenestrated flap contain elastic.

9. The protective diapering system of claim 1 wherein said anterior flap has a thickness and said posterior flap has a thickness, and the thickness of said anterior flap is greater than the thickness of said posterior flap.

10. A protective diapering system, comprising:

a) a diaper having an outer surface and an inner surface, and having an anterior flap and a posterior flap which intersect at a midline;

b) a fenestrated flap disposed between said anterior flap and said posterior flap and attached to said inner surface approximate said midline, said fenestrated flap having an anterior surface, a pair of lateral sides, and a first pair of pulling tabs secured to said pair of lateral sides, said first pair of pulling tabs formed from non-adhesive material;

c) a second pair of pulling tabs each secured to an opposite side of said anterior flap, said second pair of pulling tabs formed from non-adhesive material; and d) a pair of inner securing tabs and a pair of outer securing tabs secured to said posterior flap and coaxially aligned to one another, said pairs of inner and outer securing tabs constructed from coupling material, said pair of inner securing tabs engaging with said anterior surface of said fenestrated flap to secure said posterior flap thereto, and said pair of outer securing tabs engaging with said anterior flap to secure said posterior flap thereto and thereby secure said diaper to a male user.

11. The protective diapering system of claim 10 wherein said fenestrated flap is configured with a fenestration capable of receiving a male user's genital area when said protective diapering system is worn by the male user.

12. The protective diapering system of claim 10 wherein said diaper has an hour glass shape and said fenestrated flap has a half hour glass shape.

13. The protective diapering system of claim 10 wherein said pair of lateral sides of said fenestrated flap contain elastic.

14. The protective diapering system of claim 10 wherein said anterior flap has a thickness and said posterior flap has a thickness, and the thickness of said anterior flap is greater than the thickness of said posterior flap.

15. The protective diapering system of claim 10 wherein said anterior flap contains a greater amount of absorbent material than said posterior flap.

16. A protective diapering system, comprising:

a) a diaper having an outer surface and an inner surface, and having an anterior flap and a posterior flap which intersect at a midline;

b) a fenestrated flap disposed between said anterior flap and said posterior flap and attached to said inner surface along a line offset from said midline, said fenestrated flap having an anterior surface, a pair of lateral sides, and a first pair of pulling tabs secured thereto, said first pair of pulling tabs formed from non-adhesive material, said fenestrated flap having a fenestration configured to receive a male user's genital area, and said fenestrated flap forming a first chamber adjacent to said anterior flap and a second chamber adjacent to said posterior flap;

c) a second pair of pulling tabs each secured to an opposite side of said anterior flap, said second pair of pulling tabs formed from non-adhesive material; and d) a pair of inner securing tabs and a pair of outer securing tabs secured to said posterior flap and coaxially aligned to one another, said pairs of inner and outer securing tabs constructed from coupling material, said pair of inner securing tabs engaging with said anterior surface of said fenestrated flap to secure said posterior flap thereto, and said pair of outer securing tabs engaging with said anterior flap to secure said posterior flap thereto and thereby secure said diaper to a male user, and wherein the male user's genital area extends into said first chamber and stool discharged by the male user is retained in the second chamber and is prevented from migrating to said first chamber by said fenestrated flap.

17. The protective diapering system of claim 16 wherein said first pair of pulling tabs is designed to be tucked behind the male user's posterior once said fenestrated flap is drawn against the male user's abdomen.

18. The protective diapering system of claim 17 wherein said second pair of pulling tabs is designed to be tucked behind the male user's posterior once said anterior flap is drawn against the male user's abdomen.

19. A method for preventing stool from soiling a male's genital area during diaper use by utilizing a protective diapering system comprising a diaper having an outer surface and an inner surface, and having an anterior flap and a posterior flap; a fenestrated flap disposed between said anterior flap and said posterior flap and attached to said inner surface, said fenestrated flap having an anterior surface, a fenestration formed therethrough which is configured to receive a male user's genital area, a pair of lateral sides, and a first pair of pulling tabs secured thereto, said first pair of pulling tabs formed from non-adhesive material; said fenestrated flap forming a first chamber adjacent to said anterior flap and a second chamber adjacent to said posterior flap, a second pair of pulling tabs secured to said anterior flap, said second pair of pulling tabs formed from non-adhesive material; and a pair of inner securing tabs and a pair of outer securing tabs secured to said posterior flap and coaxially aligned to one another, said pair of inner securing tabs engaging with said anterior surface of said fenestrated flap to secure said posterior flap thereto, and said pair of outer securing tabs engaging with said anterior flap to secure said posterior flap thereto and thereby secure said diaper to a male user, said method comprising the steps of:

a) positioning an end of the male user's genital area through said fenestration and into said first chamber; and b) utilizing said fenestration flap to prevent stool discharged by the male user into said second chamber from migrating to said first chamber and contacting said genital area of said male user.

20. The method of claim 19 wherein said fenestrated flap comprises a slit and at least one fastening tab configured to bridge said slit, said method further comprising the step of securing the male user's genital area in said fenestration by securing said fastening tab across said slit.

21. The method of claim 20 further comprising the step of positioning the male user's posterior on said inner surface of said posterior flap with said anterior flap positioned between the legs of the male user, and said first pair of pulling tabs secured to said fenestrated flap.

* * * * *

UNITED STATES PATENT AND TRADEMARK OFFICE
CERTIFICATE OF CORRECTION

Page 1 of 1

PATENT NO.       : 8,870,840 B2
APPLICATION NO.  : 13/171702
DATED            : October 28, 2014
INVENTOR(S)      : Close et al.

It is certified that error appears in the above-identified patent and that said Letters Patent is hereby corrected as shown below:

In the specification

Column 4, line 64, Delete "388" between "38A," and "of" and replace with --38B--.

Column 4, line 66, Delete "468" between "46A," and "of" and replace with --46B--.

Column 8, line 66, Delete "all" between "and" and "inner" and replace with --an--.

In the claim

Column 9, line 30, Claim 5, Delete "aim" between "of" and "1" and replace with --claim--.

Signed and Sealed this
Third Day of March, 2015

Michelle K. Lee
*Deputy Director of the United States Patent and Trademark Office*